(12) United States Patent
Miller et al.

(10) Patent No.: US 11,373,553 B2
(45) Date of Patent: Jun. 28, 2022

(54) DYNAMIC HAPTIC ROBOTIC TRAINER

(71) Applicant: The Penn State Research Foundation, University Park, PA (US)

(72) Inventors: Scarlett Miller, State College, PA (US); Jason Z. Moore, State College, PA (US); David Han, Hummelstown, PA (US); Katelin Mirkin, Hummelstown, PA (US); David Pepley, Johnstown, PA (US); Mary Yovanoff, State College, PA (US); Inki Kim, Charlottesville, VA (US)

(73) Assignee: The Penn State Research Foundation, University Park, PA (US)

( * ) Notice: Subject to any disclaimer, the term of this patent is extended or adjusted under 35 U.S.C. 154(b) by 729 days.

(21) Appl. No.: 16/326,502

(22) PCT Filed: Aug. 17, 2017

(86) PCT No.: PCT/US2017/047319
§ 371 (c)(1),
(2) Date: Feb. 19, 2019

(87) PCT Pub. No.: WO2018/035310
PCT Pub. Date: Feb. 22, 2018

(65) Prior Publication Data
US 2021/0043112 A1    Feb. 11, 2021

Related U.S. Application Data
(60) Provisional application No. 62/377,149, filed on Aug. 19, 2016.

(51) Int. Cl.
G09B 23/28    (2006.01)
A61B 34/10    (2016.01)
(Continued)

(52) U.S. Cl.
CPC ............ G09B 23/286 (2013.01); A61B 34/10 (2016.02); A61B 34/20 (2016.02); A61B 34/35 (2016.02);
(Continued)

(58) Field of Classification Search
CPC ...... G09B 23/28; G09B 23/286; G09B 23/30; G09B 23/303; A61B 34/10; A61B 34/20;
(Continued)

(56) References Cited

U.S. PATENT DOCUMENTS 6,113,395 A    9/2000  Hon
6,785,572 B2   8/2004  Yanof et al.
(Continued)

FOREIGN PATENT DOCUMENTS

WO    2007100263 A1    9/2007
WO    2015084837 A1    6/2015
WO    2016059256 A1    4/2016

OTHER PUBLICATIONS

Britelab at Penn State "Dynamic Haptic Robotic Simulator for Central Venous Catheter insertion." In: Youtube.com, May 5, 2016 [online] [retrieved on Oct. 20, 2017 (Oct. 20, 2016)] Retrieved from the Internet <URL:https://www.youtube.com/watch?v=jlhBdT2-D-8>, entire video, especially timeline 1:09-1:53; 2:00-2:10.

(Continued)

*Primary Examiner* — Timothy A Musselman
(74) *Attorney, Agent, or Firm* — Dinsmore & Shohl LLP

(57) ABSTRACT

A haptic robotic training system includes a haptic robot arm, a position tracking system, a scanning surface, a monitor and a computer. The robotic arm includes a haptic feedback system and holds a custom syringe in place. The position tracking system includes a positon tracking probe shaped like an ultrasound probe and a motion tracker. The scanning surface is a soft pad made from a synthetic phantom tissue.

(Continued)

A simulation software receives the positioning data for the syringe from the robotic arm, and for the virtual ultrasound probe from the position tracking system and generates a virtual environment which mimics an actual ultrasound image. The user receives a real time feedback in the form of a haptic feel through the robotic arm, a virtual ultrasound image on the screen, and a performance feedback on the simulation software.

24 Claims, 6 Drawing Sheets

(51) Int. Cl.
 A61B 34/20 (2016.01)
 A61B 34/35 (2016.01)
 A61B 34/00 (2016.01)
 A61B 90/00 (2016.01)
 G09B 23/30 (2006.01)

(52) U.S. Cl.
 CPC .............. *A61B 34/76* (2016.02); *A61B 90/37* (2016.02); *G09B 23/303* (2013.01); *A61B 2034/104* (2016.02); *A61B 2034/105* (2016.02); *A61B 2034/2063* (2016.02); *A61B 2090/378* (2016.02)

(58) Field of Classification Search
 CPC ......... A61B 34/35; A61B 34/76; A61B 90/37; A61B 2034/104; A61B 2034/105; A61B 2034/2063; A61B 2090/378
 See application file for complete search history.

(56) References Cited

U.S. PATENT DOCUMENTS

| | | |
|---|---|---|
| 8,297,983 B2 | 10/2012 | Savitsky et al. |
| 8,480,404 B2 | 7/2013 | Savitsky |
| 10,290,231 B2 * | 5/2019 | Rios ..................... G09B 23/285 |
| 2004/0009459 A1 * | 1/2004 | Anderson ............... G06T 19/00 434/262 |
| 2009/0216191 A1 | 8/2009 | Loeffel et al. |
| 2009/0221908 A1 | 9/2009 | Glossop |
| 2009/0253109 A1 | 10/2009 | Anvari et al. |
| 2009/0299711 A1 | 12/2009 | Rosenberg |
| 2011/0301500 A1 | 12/2011 | Maguire et al. |
| 2013/0065211 A1 | 3/2013 | Amso et al. |
| 2013/0280685 A1 | 10/2013 | Patrickson et al. |
| 2013/0323700 A1 * | 12/2013 | Samosky ............... G09B 23/28 434/262 |
| 2016/0104393 A1 | 4/2016 | Savitsky et al. |
| 2018/0005547 A1 * | 1/2018 | Baker .................... G09B 23/30 |

OTHER PUBLICATIONS

Dong, B. et al. A Novel Method for Enhanced Needle Localization Using Ultrasound-Guidance, UCLA CAM Report 08-65.2008.
Gordon, A et al. "Needle insertion force model for haptic simulation" Proceedings of the ASME 2015 International Manufacturing Science and Engineering Conference, MSEC2015.
YouTube video entitled "Graduate Student Collaboration: Designing Solutions for Real World Challenges" Published on May 2, 2016; URL: <https://www.youtube.com/watch?v=aPt4VYBnr04>.
DHRT Final Video; located at URL: <https://psu.app.box.com/s/2sf8jj0s9enu5zx8ymyupxspysbncgvu>.

* cited by examiner

DYNAMIC HAPTIC ROBOTIC TRAINER

REFERENCE TO RELATED APPLICATION

This application is a U.S. national stage of PCT/US2017/047319, filed Aug. 17, 2017, which claims priority from U.S. Provisional Patent Application Ser. No. 62/377,149, filed Aug. 19, 2016, the entire content of both of which is incorporated herein by reference.

GOVERNMENT SUPPORT

This invention was made with government support under Grant No. HL127316, awarded by the National Institutes of Health. The Government has certain rights in the invention.

FIELD OF THE INVENTION

This invention relates to a medical training system, in particular, a dynamic haptic robotic training system.

BACKGROUND OF THE INVENTION

Central venous catheterization (CVC) is a medical procedure where a surgeon attempts to place a catheter in the jugular, subclavian, or femoral vein. While useful, this procedure places patients at risk of a wide variety of adverse effects. Traditionally, training is performed on CVC mannequins. These traditional CVC training systems range from low-cost homemade models to "realistic" manikins featuring an arterial pulse and self-sealing veins (e.g. Simulab CentralLineMan controlled through a hand-pump). While these "realistic" simulators allow multiple needle insertion and practice trials without consequence, they are static in nature and may not vary patient anatomy.

SUMMARY OF THE INVENTION

The present invention provides a central venous catheterization (CVC) haptic robotic training simulator. Training of any procedure that requires the dexterous manipulation of a tool and/or the precise positioning of an ultrasound probe may benefit from the present invention. This includes procedures besides CVC including but not limited to spinal access procedures (epidural, lumbar drain, etc.), vein or artery access in the body (minimally invasive treatment of artery disease, blood drawing, fluid delivery, etc.), diagnostic ultrasound based procedures (echocardiogram, musculoskeletal exams, urological exams, etc.), disease treatment procedures (cryotherapy, brachytherapy, etc.), biopsy procedures, laparoscopic procedures, marker placement procedures, and anesthesiology to train for guiding a needle to precise positions in the body.

The haptic robotic training simulator, also referred to as a virtual haptic training system, may include a haptic robotic arm having a holster and a simulated tool attached to the holster of the robotic arm. In one embodiment, the simulated tool is a simulated syringe.

The haptic robotic arm may be operable to provide position data to the system thereby providing the position of the simulated tool. The haptic robotic arm may also be operable to provide force feedback to a user.

The haptic robotic training simulator may include a scanning surface for the user to perform a virtual medical procedure and a virtual tool manipulation, such as a virtual ultrasound probing and a virtual needle insertion.

In one embodiment, a position tracking sensor system includes a position tracking probe and a motion tracker.

In one embodiment, the haptic robotic arm, the scanning surface and the motion tracker each have a home position. After use, the positions of the haptic robotic arm, the scanning surface and the motion tracker may be zeroed by going back to their respective home position.

The position tracking probe may include a position sensor for sensing the position of the position tracking probe. The motion tracker may include a receiver and a transmitter to communicate with the position tracking probe and determine the position of the position tracking probe relative to its home position.

The haptic robotic training simulator may include a monitor for displaying a virtual image, such as a virtual ultrasound image.

The haptic robotic training simulator may include a simulation software for simulating the virtual image associated with the virtual tool manipulation using the position of the simulated tool from the haptic robotic arm and the position of the position tracking probe from the position tracking system and providing performance feedback to the user.

The simulated syringe may include a syringe compartment, a retractable needle at a distal end of the syringe, and an extendable plunger at a proximal end of the syringe. The needle may be operable to retract into the syringe compartment when pushed against a surface and the plunger may be operable to be pulled back for simulating aspiration of the syringe.

In one embodiment of the virtual haptic training system, the position tracking probe includes a shell that mimics a real ultrasound probe.

The present invention provides a method for a virtual haptic training. The method provides a virtual haptic training system including a haptic robotic arm having a holster with a simulated tool attached, a position tracking system including a virtual ultrasound probe and a motion tracker, a scanning pad having a surface for the user to perform virtual ultrasound probing and virtual tool manipulation, a monitor for display; and a computer having a simulation software.

The haptic robotic arm may provide position data of the simulated tool to the system and force feedback to a user.

The method may include the step of performing a virtual tool manipulation by moving the simulated tool across the scanning surface and engaging the surface of the scanning pad and providing the position of the simulated tool by the haptic robotic arm during the performing of the virtual tool manipulation;

The method may include the step of performing a virtual ultrasound probing across the surface of the scanning pad and providing the position of the virtual ultrasound probe by the position tracking system during the performing of the virtual ultrasound probing.

The method may include the step of simulating a virtual ultrasound image associated with the virtual tool manipulation using the position of the simulated tool and the position of the virtual ultrasound probe and displaying a virtual ultrasound visualization associated with the virtual tool manipulation on the monitor and providing performance feedback to a user.

In one embodiment, the simulated tool is a simulated syringe including a syringe compartment, a retractable needle at a distal end of the syringe compartment, and an extendable plunger at a proximal end of the syringe compartment. The needle is operable to retract into the syringe compartment when pushed against a surface and the plunger is operable to be pulled back for simulating aspiration of the syringe. In this embodiment, the virtual tool manipulation is virtual needle insertion.

In one embodiment, the scanning pad is made from phantom tissue. The retractable needle engages and anchors in the phantom tissue when pushed against the phantom tissue. The phantom tissue is compressible when pushed against by the retractable needle and the virtual ultrasound visualization shows the compression.

In one embodiment, the haptic force feedback is generated using a combination of position tracking and a force characterization of the virtual needle insertion which characterizes needle insertion force as a piecewise exponential function.

In one embodiment, the virtual ultrasound visualization is a virtual environment created based on a number of actual ultrasound images. The virtual environment may include a background of the virtual ultrasound created as a static compilation of ultrasound images taken from a region around a vein.

In this embodiment, the virtual environment includes two circles and virtual vessel images are created by overlaying the images of an artery and the vein onto the circles providing images of a virtual vein and a virtual artery.

In one embodiment, rotating and moving the virtual ultrasound probe allows a user to navigate the virtual environment and rotating and moving the virtual ultrasound probe causes the virtual vessel images to move in a realistic fashion.

In this embodiment, pressing the virtual ultrasound probe into the scanning pad surface causes the virtual vein to compress, thereby simulating a real ultrasound procedure and the virtual artery image has a pulsatile nature to represent a heartbeat.

In this embodiment, a series of horizontal deformation lines that flex represent the tissue deformation during a real needle insertion when the retractable needle is pushed against and engages the scanning pad surface and a virtual needle tip in the virtual environment represents a location of the virtual needle tip after insertion. The virtual vein shows deformation at a contact region depending on the location of the virtual needle tip when the virtual needle tip comes in contact with the virtual vein by manipulating the circumferential points that form the circle. The virtual vein is differentiated from the virtual artery by checking their respective compressibility.

In one embodiment, a colored bar appears on the virtual image representing blood flash when the virtual need enters a virtual vessel, the color depending on whether the virtual vessel is the virtual vein or virtual artery.

In one embodiment, the holster of the virtual ultrasound probe, the scanning pad and the haptic robotic arm are fixed to a platform and the holster of the virtual ultrasound probe, the scanning pad and the haptic robotic arm each have a home position.

DETAILED DESCRIPTION OF THE INVENTION

Figure 1:
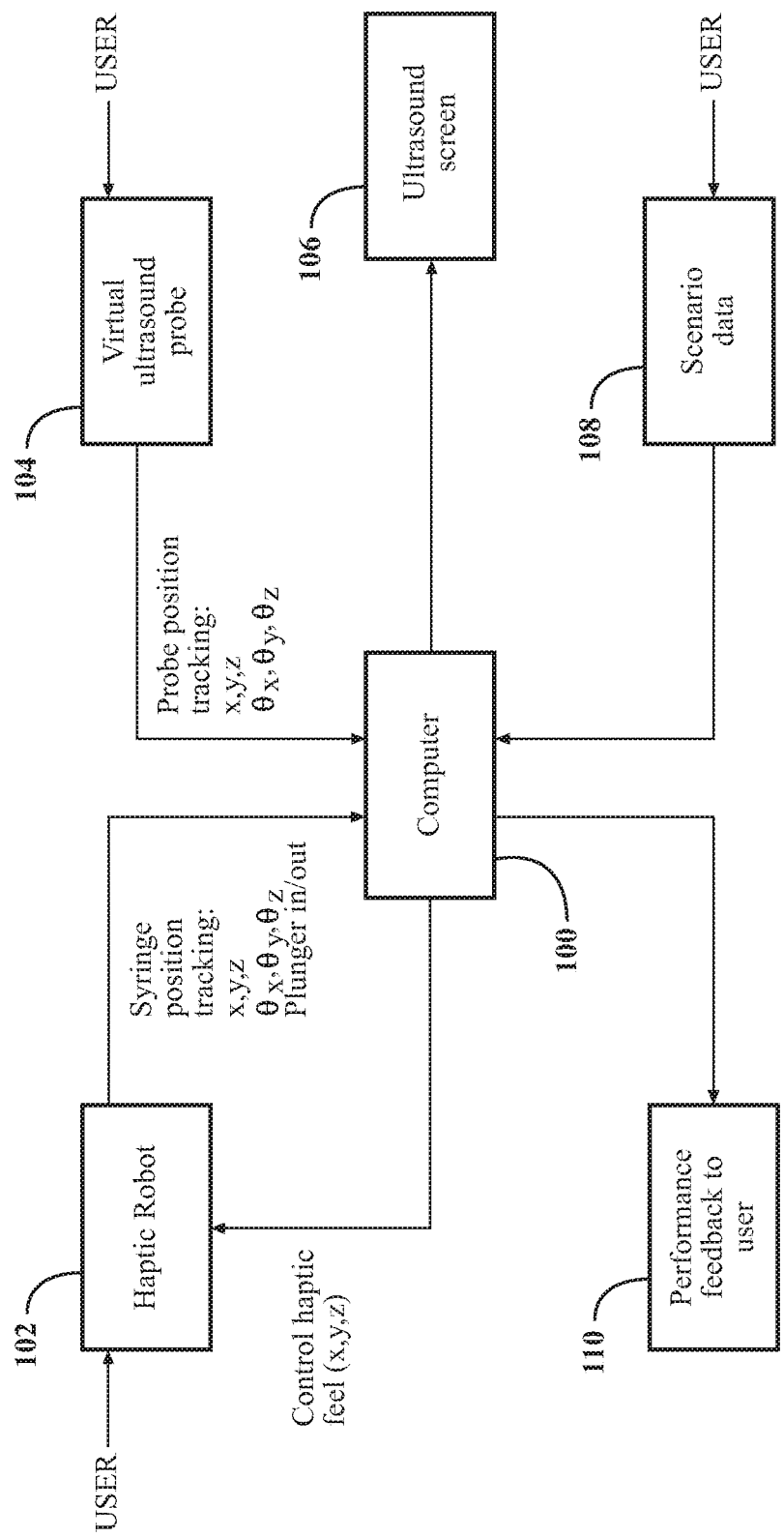
FIG. 1 is a schematic view showing a concept of operations of a system in accordance with an embodiment of the present invention.

The present invention provides a central venous catheterization (CVC) haptic robotic training simulator. The simulator is also called a Dynamic Haptic Robot Trainer (DHRT). Referring to FIG. 1, the design of the DHRT includes two components: a haptic feedback robot arm 102 and a virtual ultrasound probe 104. The DHRT further includes a ultrasound screen 106 which may be a computer monitor and a computer 100 for running simulation software. The computer 100 also provides an interface for receiving scenario data from a user and for sending feedback information back to the user.

Figure 2:
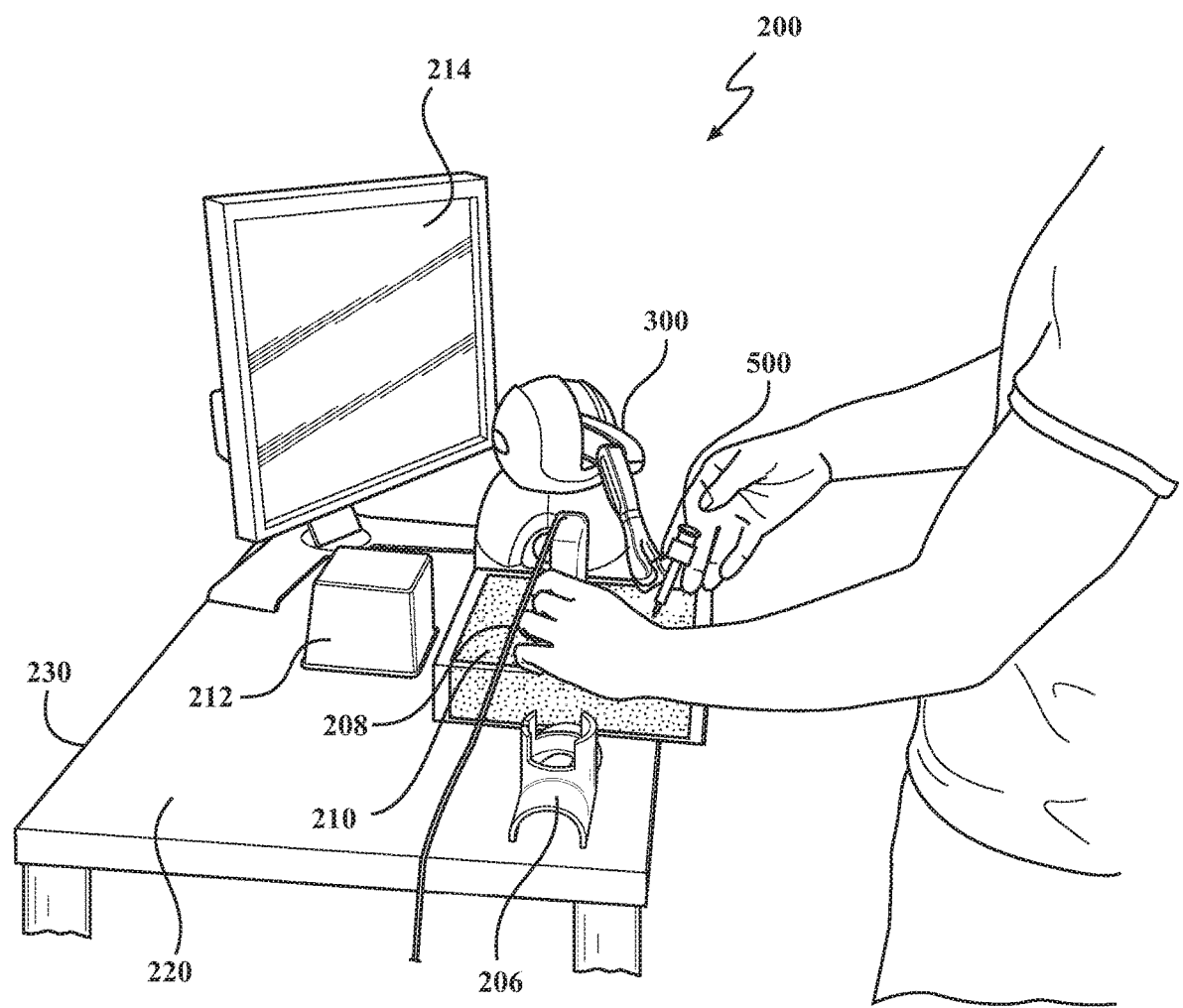
FIG. 2 is a perspective view showing a virtual reality haptic simulator mobile platform in accordance with an embodiment of the present invention.
Figure 3:
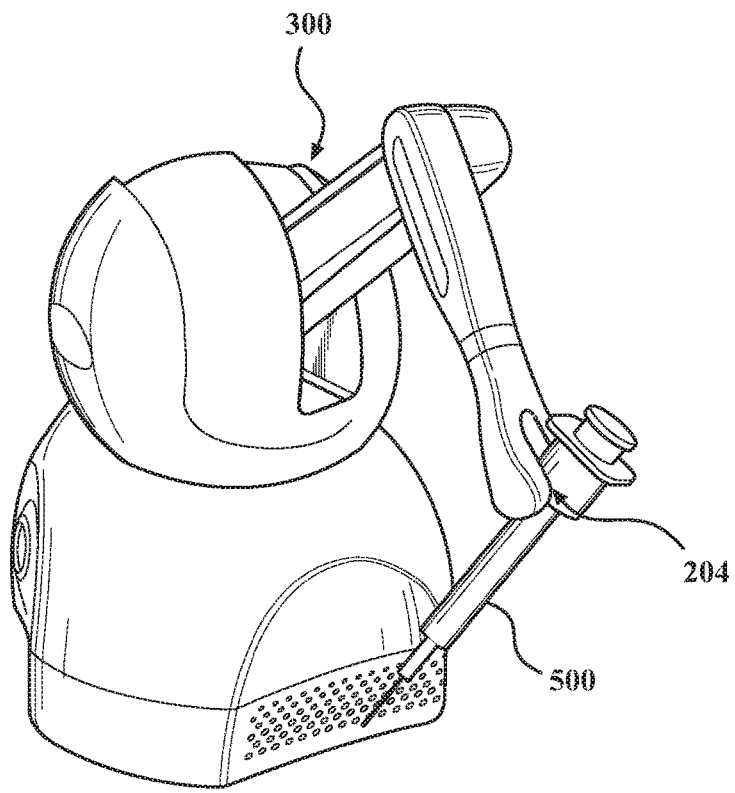
FIG. 3 is a perspective view showing a haptic robotic arm holding a custom simulated syringe attachment in accordance with an embodiment of the present invention.
Figure 4:
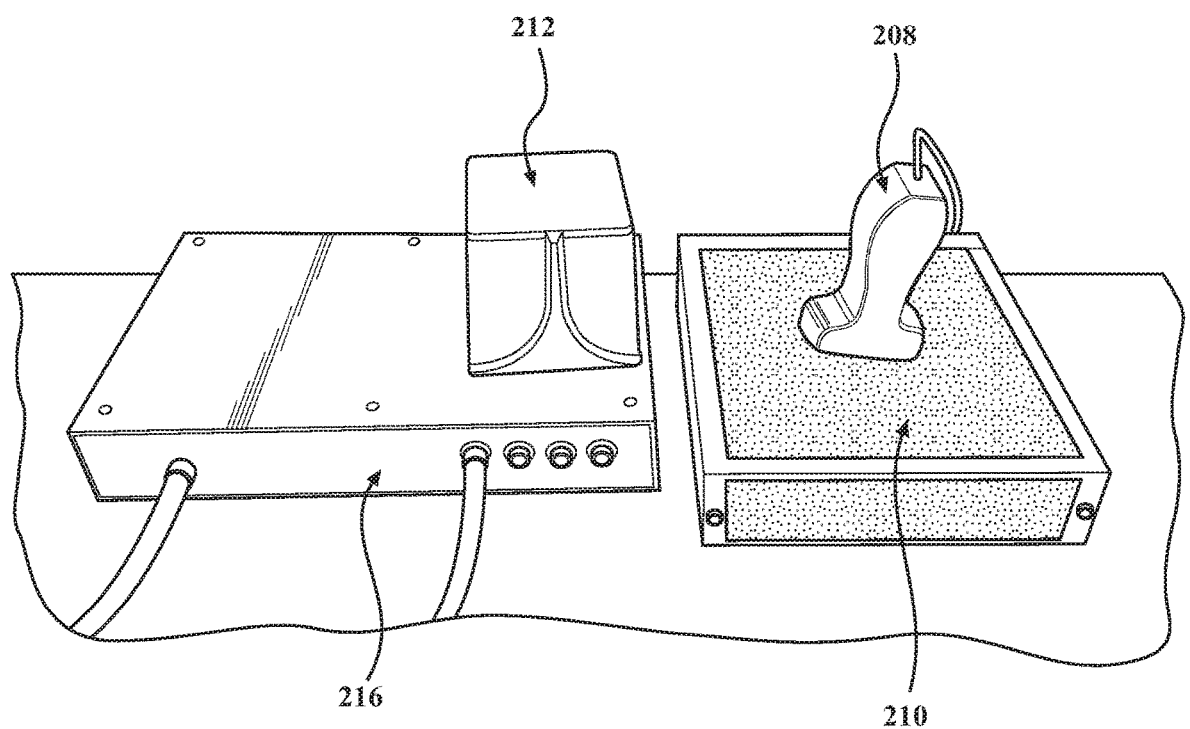
FIG. 4 is a perspective view showing a virtual ultrasound probe, a phantom tissue scanning surface, and a position tracker in accordance with an embodiment of the present invention.

The haptic robot arm 300 is customized with a bolster 204 used to hold a simulated syringe 500 in place, as shown in FIGS. 2 and 3. The haptic robot provides a haptic feedback system and the position of the simulated syringe. An example of the haptic feedback system is a 3D Systems Geomagic Touch. The haptic robot consists of three rotary encoders, along with the arm dimensions to determine the position of the simulated syringe needle. The virtual ultrasound probe 208 utilizes a position tracking system as the foundation for controlling the virtual ultrasound. The position tracking system may be an electromagnetic position tracker. An example is an Ascension 3D Guidance trakSTAR, including a motion tracker transmitter/receiver 212 and a position tracking probe 208. The position tracking probe may be outfitted with a custom 3D printed ultrasound probe shell, as shown in FIG. 4. The custom 3D printed ultrasound probe may mimic the shape and appearance of a real ultrasound probe to familiarize users with the feel of an actual ultrasound probe. In certain embodiments, the tracking probe has 6 degrees of position tracking with an accuracy of 1.4 mm RMS and 0.5 degrees RMS. A scanning surface 210 mimicking a skin layer may be provided for the users to manipulate the virtual ultrasound probe on. The scanning surface 210 may be a soft pad made from phantom tissue, providing a compressible, realistic feeling scanning surface for the ultrasound. This scanning surface 210 also allows for the simulated syringe to be anchored into the tissue by a few millimeters. This anchoring prevents the user from being able to move the simulated syringe sideways when it is simulated as being inside the tissue. The highly accurate probe position magnetic tracking sensor can determine based on probe position when the ultrasound pad is being compressed because the position of the ultrasound pad is fixed in place. This information is then sent to the computer to appropriately modify the virtual ultrasound visualization to simulate visualizing compressed tissue. The synthetic phantom tissue utilized in one example is made of polyvinyl chloride modified with plastisol (M-F Manufacturing). This inexpensive material can be molded to any shape to simulate non-planar surfaces that would be present on an actual body, is synthetic (not animal based) so it will not rot, and can be modified using softener compound to properly simulate the stiffness feeling of the tissue. This system can also allow for the use of an actual human rather than a synthetic pad to realistically simulate the surface of the body that is being scanned and the patient interaction that occurs during these procedures. Alternative phantom tissue materials may also be used.

A simulated syringe is one of the numerous tools that could be affixed to the haptic robotic arm 300. Any tool that requires the dexterous movement of the physician including but not limited to a syringe, needle, tube, guidewire, dilator, catheter, laparoscopic instrument, scalpel, drill, and saw could be affixed to the robotic arm. Similarly the simulated ultrasound probe can be made to be any of the numerous imaging device shapes utilized in specific procedures that require the positioning of an imaging device.

Referring to FIGS. 1 and 2, an exemplary operation of the DHRT will be described.

The haptic robotic arm 300, the motion tracker 212, and the testing surface pad 210 are physically mounted to a board 200. A home position is provided outside of the phantom tissue testing surface pad for each of the components secured to the board so that the user puts the needle and the ultrasound probe back in the same position before every trial. This is for the purpose of zeroing the position of the sensors. In one embodiment, when the motion tracker is in its home position, the position tracking probe is in its home position. For example, when the position tracking probe is returned to its holster, the position tracking probe and the motion tracker are in their home positions.

In this example, the user ensures that the hand held virtual ultrasound probe 208 and haptic robotic arm 300 are in their respective home positions. The user selects the desired medical scenario from the available options in the simulation software. The user controls the probe and simulated syringe to perform the task required, as shown in FIG. 2. The simulation software generates a virtual ultrasound environment which resembles an actual ultrasound image as if the user is actually performing the simulated task. The simulation software has the capability to generate a variety of scenarios. The simulation software receives its 3D positioning data for the simulated syringe 500 from the series of encoders in the haptic robotic arm 300, and for the virtual ultrasound probe 208 from the magnetic position tracker, and simulates the needle insertion which can be seen on the virtual ultrasound image on the ultrasound screen 106. With the help of an electrical switch 506 in the simulated syringe 500, the haptic robotic arm 300 also provides simulated syringe excursion data to the software. When a simulated needle insertion is performed, the simulation software also computes the haptic feedback with the position of the virtual ultrasound probe, the position of the needle tip 508, the angle of the needle, final distance from the needle to the vein center and simulated syringe excursion inputs from the hardware. The haptic feedback can be analyzed to detect known problematic procedure behaviors such as multiple insertion attempts. The DHRT allows users to receive real time feedback in the form of a haptic feel through the robotic arm, a virtual ultrasound image on the screen, and a performance feedback on the simulation software.

Figure 5:
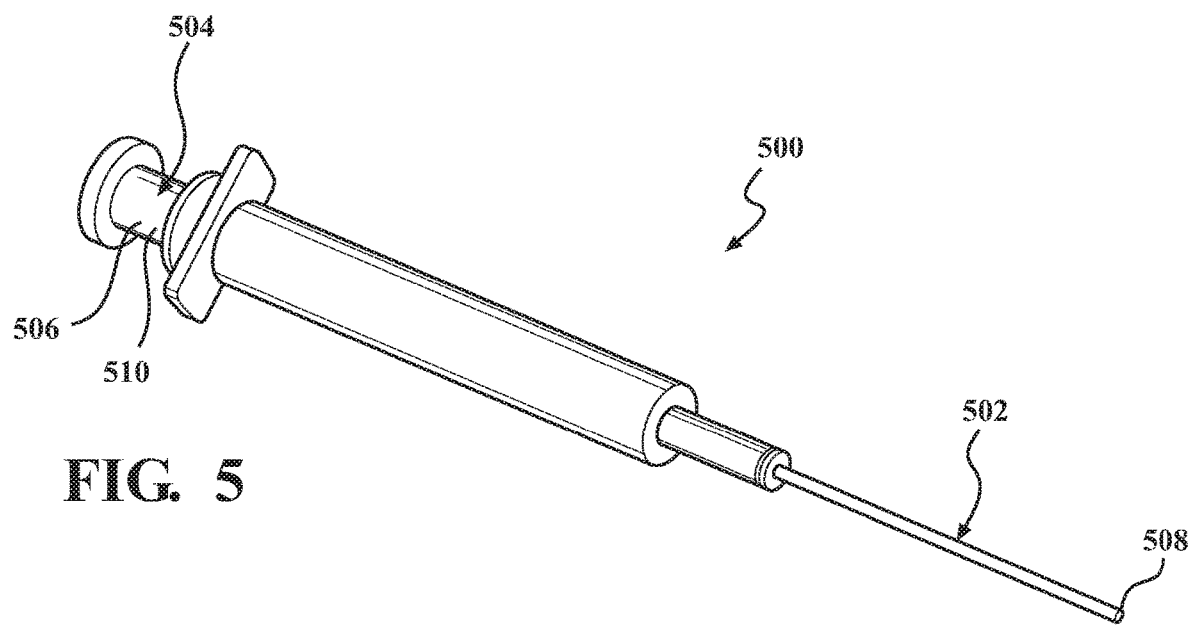
FIG. 5 is a perspective view showing a custom simulated syringe attachment in accordance with an embodiment of the present invention.

As shown in FIG. 5, the simulated syringe includes a retractable needle 502 and an extendable plunger 504. In one example, three compression springs are attached in series to the needle and have a spring rate of 0.508 N/cm, giving them enough force to extend the needle, but provide minimal force feedback to the user. The plunger 504 includes a sensor 510 that senses the pullback negative pressure when the user is aspirating the simulated syringe and then the plunger 504 activates a switch 506, providing the program with the excursion data of the simulated syringe.

The extendable plunger of the simulated syringe attachment plays an important role in the simulation. During CVC insertion, the surgeon must be constantly aspirating the simulated syringe. It is called a flash when blood fills the syringe. If the surgeon is not aspirating during vessel puncture, blood will not fill the simulated syringe, i.e., no falsh, and it is very easy to puncture the posterior wall of the vessel. Flash also helps the surgeon to know if they inserted into either the internal jugular (IJ) or a carotid artery (CA) because the deoxygenated blood seen during a flash from the IJ is darker than the oxygenated blood in the CA. The action of aspirating the simulated syringe while inserting is difficult because it involves pulling back the plunger while pushing the simulated syringe forward. Finding an insertion grip that allows the trainee to properly aspirate is an important task of the simulator.

The haptic robotic arm applies forces in response to the movement and depth of the needle, and the excursion of the simulated syringe. The haptic feedback is generated by three servomotors. The net force generated in the three primary Cartesian directions is determined by the "depth" of the needle in the tissue and a formula is used to represent forces on a needle during tissue insertion. The needle portion of the simulated syringe actual retracts rather than penetrating deeply into the phantom tissues, so the "depth" is the virtual depth. In certain embodiments, the retracting needle does penetrate the phantom tissue enough that the needle is anchored, thereby preventing the user from moving laterally or torquing the needle in an unrealistic fashion. The needle insertion force has been modeled based on the stiffness force of the tissue and the friction force that acts on the needle. Because the retractable needle does not penetrate or only penetrate the phantom tissue enough to contact, push on and engage the phantom tissue, the retractable needled is therefore useable with the surface of the phantom tissue to enhance the simulation. Because the synthetic phantom tissue is compressible and can be penetrated just enough to anchor a retractable needle, it provides a realistic feeling to the user when pushed on by a retractable needle against the surface of the testing pad, similar to the feeling when performing a real needle insertion on a human skin. Likewise, because the synthetic phantom tissue is compressible, it provides a realistic feeling to the user when pushed on by a virtual ultrasound probe against the surface of the testing pad, similar to the feeling when performing a real ultrasound probing on a human skin.

The haptic feedback for the simulation may be provided by a 3D Systems Geomagic Touch haptic robot arm. Other similar devices may be used. The 3D Systems Geomagic Touch provides 6 degrees of position tracking with 0.055 mm of position resolution and 3 degrees of force feedback in the x, y, z directions. In one example, the robotic device is controlled through Matlab® and Simulink® using the Quanser Quare (Markham, ON) software package.

In certain embodiments, the force values of the haptic feedback are generated using a combination of position tracking and a needle insertion force characterization created by Gordon et al. [1] which characterize needle force as a piecewise exponential function. The Gordon characterization of needle insertion force uses an algorithm to convert experimentally measured needle insertion force and insertion depth data into a useful piecewise function that is easy to implement into the haptic robotic program. The general form of this is shown in equation 1 where $A_n$, $B_n$, $C_n$, and $D_n$ are the characterization function parameters, x is the needle depth, and P is the piecewise intervals in terms of needle depth.

$$F(x) = \begin{cases} A_1 e^{B_1(x-D_1)} + C_1 & \text{if } 0 \le x \le P_1 \\ A_2 e^{B_2(x-D_2)} + C_2 & \text{if } P_1 \le x \le P_2 \\ \vdots & \vdots \\ A_n e^{B_n(x-D_n)} + C_n & \text{if } P_1 \le x \le P_n \end{cases} \quad (1)$$

This approach is able to capture the repeated buildup and rapid release of force experienced during needle insertion. The Gordon characterization is also highly customizable. The accuracy of the characterization can be increased by increasing the number of piecewise intervals. It is capable of converting both experimentally and artificially generated needle force and depth data into easy to implement functions. This customizability makes creating realistic needle insertion force scenarios simple. In addition to the forces generated through the Gordon characterization, small bounding forces are applied in the directions radial to the axis of insertion once the virtual skin has been entered. This helps to prevent the user from moving laterally or torquing the needle in an unrealistic fashion.

In certain embodiments, the tracking device uses C++ and is interfaced with Simulink using the Quare software. The virtual ultrasound environment for this embodiment was created using Virtual Reality Modeling Language (VRML) due to its compatibility with Simulink. The creation of the virtual ultrasound image begins with visualization of 3D space as a 2D cutting plane. Like a true ultrasound, the 2D image seen in the virtual ultrasound is the 2D cross section of the virtual beam plane projected out of the end of the mock ultrasound probe. As shown in FIGS. 6A-6B and 7A-7D, there are four main objects in the VRML ultrasound environment: the background, a vein, an artery, and a rectangle representing the location where the needle crosses the ultrasound plane. The U and CA are represented by two circles in the VRML virtual world, with 16 circumferential reference points. These reference points can then be scaled in the x and y directions to vary the shapes and sizes of the vessels and allow for deformation in the vessel shape. Using the rotation of the 3D tracking device for reference, the images of the vessels stretch in the x and y directions. The needle can then interact with the position of these data points to simulate vessel flexibility. Virtual patient anatomy can be varied by moving the vessel positions in the virtual tissue.

Moving the virtual ultrasound probe 208 allows the user to navigate this virtual environment. Rotating and moving the virtual ultrasound probe causes the 2D images of the vessels to move in a realistic fashion. Pressing the virtual ultrasound probe 208 into the scanning surface 210 causes the U to compress just like it would on a real ultrasound. The artery has a slight pulsatile nature in the image to represent a heartbeat.

An important component of the ultrasound is the visualization of the needle crossing the ultrasound plane. Being able to see the needle on the ultrasound screen is an important aspect of using the ultrasound to guide the needle towards the target vein. A line projected by the needle, as seen in FIG. 7C, represents the needle in the virtual space. The ultrasound plane is represented by a point at the position of the tracker and a plane normal vector projected from this point. Using the needle line and ultrasound plane, the 3D line-plane intersection can be found. Then, using the linear transformation in Eq. (2) the intersection point on the 2D ultrasound image is found, where T is a 2×3 transformation matrix consisting of the x-axis and y-axis vectors in 3D space, I is the 3D location of the needle plane intersection, and p is the 3D location of the ultrasound probe. Finally, $x_{new}$ and $y_{new}$ are the resulting intersection locations on the ultrasound plane, represented by a small rectangle in the previously created ultrasound virtual world.

$$\begin{bmatrix} x_{new} \\ y_{new} \end{bmatrix} = T \begin{bmatrix} I_x - p_x \\ I_y - p_y \\ I_z - p_z \end{bmatrix} + \begin{bmatrix} p_x \\ p_y \end{bmatrix} \quad (2)$$

The textures used on the objects in the virtual ultrasound image are based on several actual ultrasound images of the region around the right U and CA. The background of the ultrasound was created as a static compilation of ultrasound images taken from the region around U procedures. These images were blended to give a generic yet realistic look. Overlaid on the virtual vessels were images of a CA and IJ. These were cropped to fit the vessels in the image.

Figure 6A:
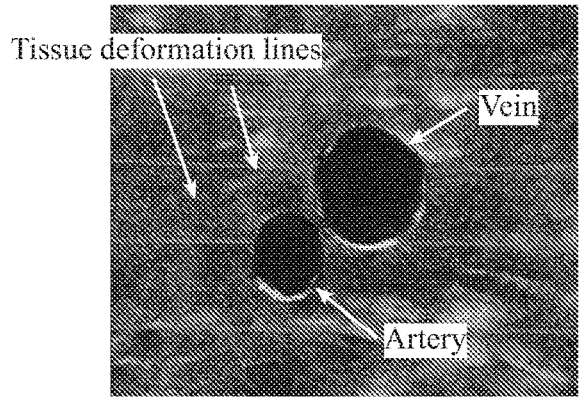
FIG. 6A is a view of a virtual ultrasound image of an internal jugular (U) and a carotid artery (CA)
Figure 6B:
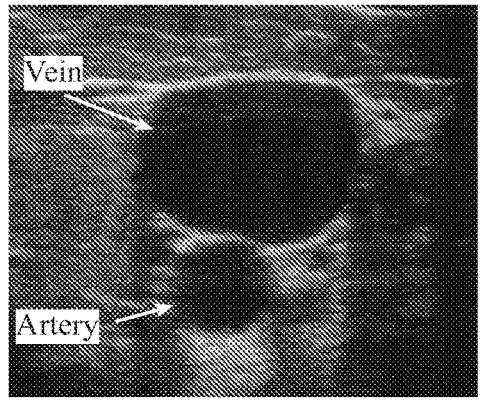
FIG. 6B is a view of an actual ultrasound image of an U and a CA.
Figure 7A:
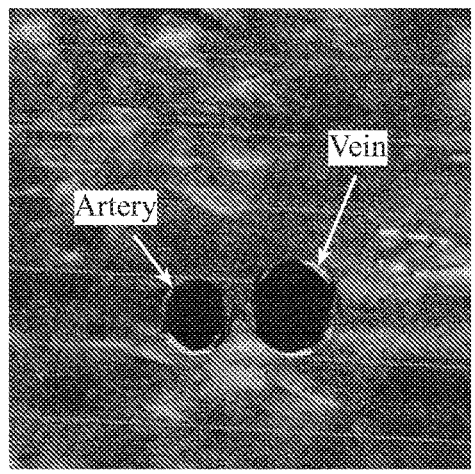
FIG. 7A is a view of a virtual ultrasound image during the finding vessels stage.
Figure 7B:
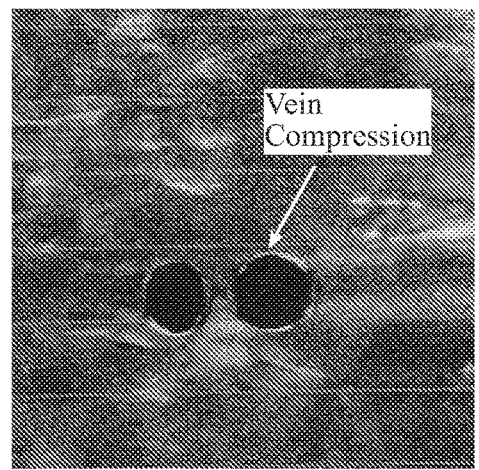
FIG. 7B is a view of a virtual ultrasound image during the stage of finding a vein by checking the compressibility.
Figure 7C:
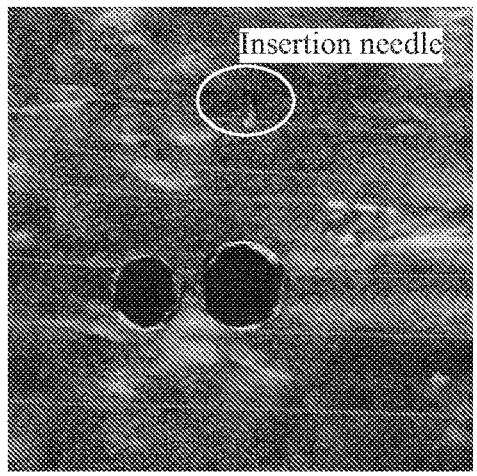
FIG. 7C is a view of a virtual ultrasound image during the stage of identifying where the needle crosses the ultrasound plane.
Figure 7D:
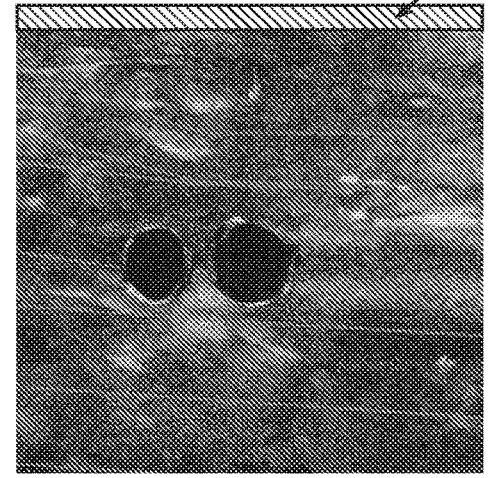
FIG. 7D is a view of a virtual ultrasound image during the stage of vein deformation and a flash appears during successful insertion.

As shown in FIGS. 6A and 7B, the haptic robotic arm is also able to deform objects in the virtual ultrasound. When the needle enters the tissue, there is a series of horizontal deformation lines that flex to represent the tissue deformation that would be seen during an actual insertion. When the virtual needle tip comes in contact with the virtual vein, the vein deforms realistically depending on where it is touched by the virtual needle. This is done by manipulating the 16 circumferential points that form the circle depending on the location of the needle tip. The vein can be differentiated from the artery by checking the compressibility since veins compress more than arteries when compressed. Finally, as seen in FIG. 7D, if the user is aspirating the needle when the needle enters a vessel, a colored bar representing blood flash will appear on screen. This bar may be blue if they enter the vein and red if they enter the artery. If they are not aspirating, no flash will appear.

The virtual environment is heavily configurable to vary the difficulty of the insertion. The locations, sizes, and shapes of the two vessels am modifiable. This combined with a variety of haptic feedback characterizations allows the user to attempt a wide variety of insertion scenarios ranging from a morbidly obese patient to the presence of scar tissue. When all of these features are combined, an effective virtual ultrasound environment is formed.

The illustrated embodiment of the virtual haptic robotic simulator was designed to be mobile for easy transportability around its training center, as shown in FIG. 2. The system is based on a large plastic push cart 230. Plastic was used to avoid any possible interference with the electromagnetic position tracker. A large acrylic glass surface 220 was mounted on top of the cart as a testing surface. Affixed to this surface is a computer monitor 214 used for navigating the computer program and the ultrasound image, the motion tracker transmitter 212, the haptic robotic arm 300, the holsters 204, 206 for the simulated syringe and probe, and finally the artificial CVC testing surface 210. The testing surface pad is placed in the middle of the acrylic glass surface. The lower portion of the cart holds the PC running the simulation and the 3D Guidance trakSTAR 216. The PC uses a 3.5 GHz hex-core Intel i7 processor, with solid state storage, and 32 GB of memory to ensure that the simulation runs fast enough to feel realistic and maintain 60 frames per second on the virtual ultrasound. Other carts, hardware and software may be used.

A consistent position based calibration of the devices was achieved by physically mounting the haptic robotic arm, the motion tracker, and the testing surface pad to the table. Setting each device to a known starting position, the arm, tracker, and pad interact with each other in known relative positions.

In some embodiments, the DHRT program continuously assesses the user's performance at hand control and force perception. In the DHRT system, the user goes through a specific scenario on the device and the system automatically determines the next scenario the patient needs to perform in order to maximize the learning. Based on this continuous assessment, the program dynamically guides the resident through tasks to allow them to build on their weakest strengths. The user is also given feedback from the program that tells them how well they performed on the given task. The DHRT provides quantitative assessment of user performance and allows them to learn at their own pace without consequence. This will ensure the reduction in operator-dependence errors (e.g. experience, time allotted to perform procedure, stress, fatigue) and reduce the errors associated with the relationship between simulation and practice. The DHRT provides a wide variety of anatomical scenarios to better train surgeons on complications associated with patient variability (e.g. anatomic variation, body habitus and coagulopathy) to prepare residents for the variety of patients they will encounter. The DHRT provides a standardized method for effective learning. This standardization can help ensure residents are being effectively trained and can provide regulations for CVC training and reduce the errors associated with current surgical training techniques.

Figure 8:
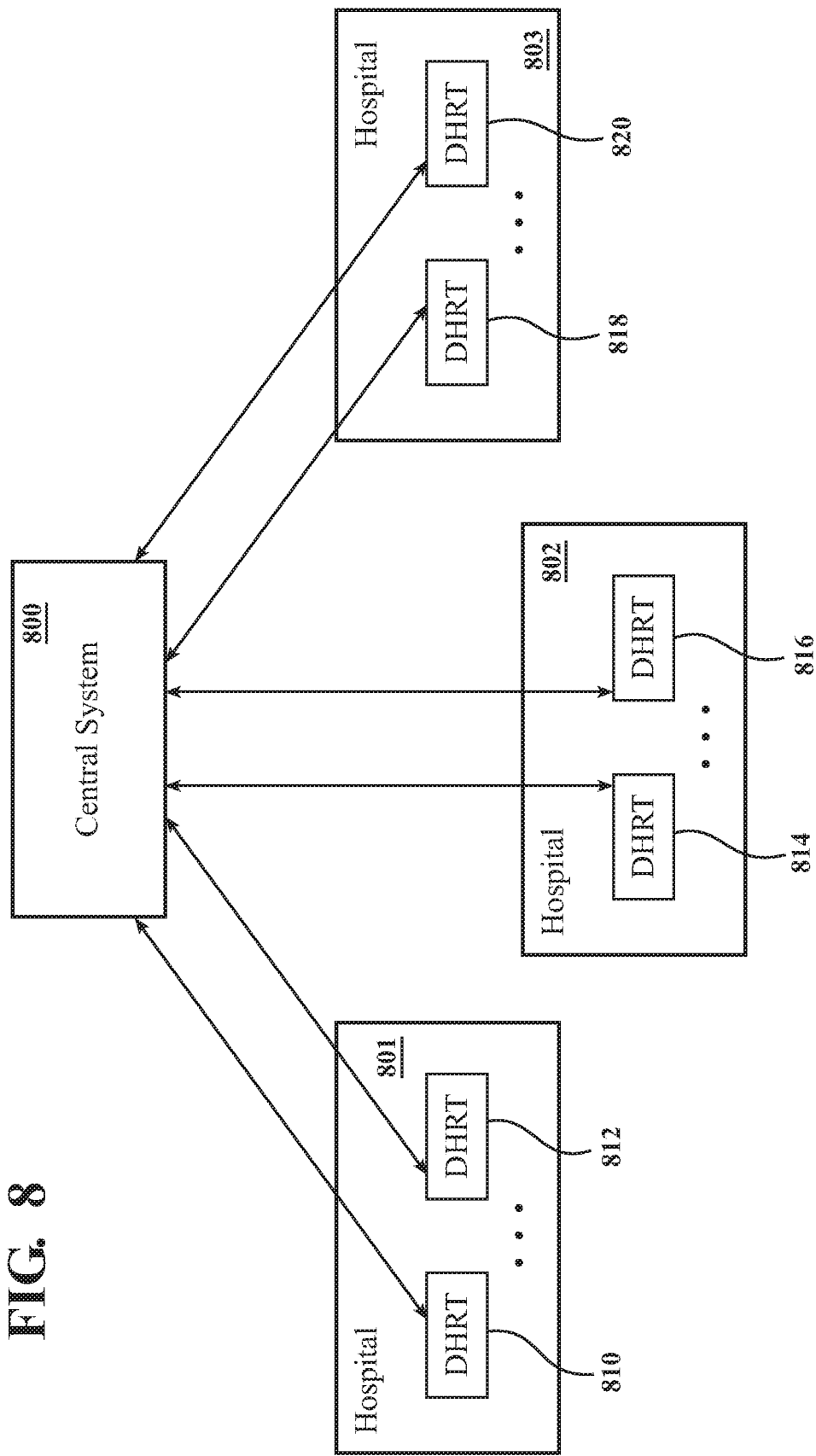
FIG. 8 is a schematic view of a system comprising multiple virtual haptic training systems communicably connected to a central system in accordance with an embodiment of the present invention.

The present system can be connected to numerous other systems that collect user data and send data to a central system to allow for continuous improvement to the learning algorithms. As shown in FIG. 8, multiple systems placed at far away hospitals can be configured to send information to a central system. This central system would collect and analyze this massive collection of data to then send out modifications of the program to the devices. This configuration allows continuous learning information to being collected and utilized to improve the learning efficiency of these devices.

As will be clear to those of skill in the art, the embodiments of the present invention illustrated and discussed herein may be altered in various ways without departing from the scope or teaching of the present invention. Also, elements and aspects of one embodiment may be combined with elements and aspects of another embodiment. It is the following claims, including all equivalents, which define the scope of the invention.

REFERENCE

[1] A. Gordon, I. Kim, B. A, and M. J, "Needle Insertion Force Model for Haptic Simulation," in *Proceedings of the ASME International Manufacturing Science and Engineering Conference*, 2015.

The invention claimed is:

1. A method for a virtual haptic training, the method comprising the steps of:
   providing a virtual haptic training system including:
      a haptic robotic arm having a holster, the haptic robotic arm providing position data to the system and force feedback to a user;
      a simulated tool, attached to the holster of the robotic arm, a position of the simulated tool tracked by the haptic robotic arm;
      a position tracking system including a virtual ultrasound probe and a motion tracker, the virtual ultrasound probe being a position tracking probe outfitted as an ultrasound probe;
      a scanning pad having a surface for the user to perform virtual ultrasound probing and virtual tool manipulation;
      a monitor for display; and
      a computer having a simulation software;
   performing a virtual tool manipulation by moving the simulated tool across the scanning surface and engaging the surface of the scanning pad;
   providing the position of the simulated tool by the haptic robotic arm during the performing of the virtual tool manipulation;
   performing a virtual ultrasound probing across the surface of the scanning pad;
   providing the position of the virtual ultrasound probe by the position tracking system during the performing of the virtual ultrasound probing;
   simulating, by the computer, a virtual ultrasound image associated with the virtual tool manipulation using the position of the simulated tool and the position of the virtual ultrasound probe; and
   displaying a virtual ultrasound visualization associated with the virtual tool manipulation on the monitor and providing performance feedback to a user,
   wherein the simulated tool is a simulated syringe having a retractable needle, the virtual tool manipulation is virtual needle insertion, and a virtual needle tip in the virtual ultrasound visualization represents a location of the virtual needle tip after insertion.

2. The method according to claim 1, wherein the scanning pad is made from phantom tissue.

3. The method according to claim 2, wherein the simulated syringe comprises:
   a syringe compartment;
   the retractable needle being disposed at a distal end of the syringe compartment, the needle operable to retract into the syringe compartment when pushed against a surface,
   an extendable plunger at a proximal end of the syringe compartment, the plunger operable to be pulled back for simulating aspiration of the syringe; and
   the retractable needle engaging and anchoring in the phantom tissue.

4. The method according to claim 3, wherein the phantom tissue is compressible when pushed against by the retractable needle and the virtual ultrasound visualization shows the compression.

5. The method according to claim 3, wherein the haptic force feedback is generated using a combination of position tracking and a force characterization of the virtual needle insertion which characterizes needle insertion force as a piecewise exponential function.

6. The method according to claim 2, wherein the virtual ultrasound visualization is a virtual environment created based on a number of actual ultrasound images.

7. The method according to claim 6, wherein the virtual environment includes a background of the virtual ultrasound created as a static compilation of ultrasound images taken from a region around a vein.

8. The method according to claim 6, wherein a series of horizontal deformation lines that flex represent the tissue deformation during a real needle insertion when the retractable needle is pushed against and engages the scanning pad surface.

9. The method according to claim 7, wherein the virtual environment includes two circles and virtual vessel images are created by overlaying the images of an artery and the vein onto the circles providing images of a virtual vein and a virtual artery.

10. The method according to claim 7, wherein rotating and moving the virtual ultrasound probe allows a user to navigate the virtual environment.

11. The method according to claim 9, wherein pressing the virtual ultrasound probe into the scanning pad surface causes the virtual vein to compress, thereby simulating a real ultrasound procedure.

12. The method according to claim 9, wherein the virtual vein shows deformation at a contact region depending on the location of the virtual needle tip when the virtual needle tip comes in contact with the virtual vein by manipulating the circumferential points that form the circle.

13. The method according to claim 9, wherein the virtual vein is differentiated from the virtual artery by checking their respective compressibility.

14. The method according to claim 9, wherein a colored bar appears on the virtual image representing blood flash when the virtual needle enters a virtual vessel, the color depending on whether the virtual vessel is the virtual vein or virtual artery.

15. The method according to claim 1, wherein:
the virtual haptic training system further includes a holster for the virtual ultrasound probe,
the holster of the virtual ultrasound probe, the scanning pad and the haptic robotic arm are fixed to a platform, and
the holster of the virtual ultrasound probe, the scanning pad and the haptic robotic arm each have a home position.

16. A virtual haptic training system, comprising:
a haptic robotic arm having a holster, the haptic robotic arm providing position data to the system and force feedback to a user;
a simulated syringe having a retractable needle, the simulated syringe attached to the holster of the robotic arm, the position of the retractable needle provided by the haptic robotic arm;
a position tracking system including a virtual ultrasound probe and a motion tracker, the virtual ultrasound probe being a position tracking probe outfitted as an ultrasound probe;
a scanning pad for the user to perform virtual ultrasound probing and virtual needle insertion;
a monitor for displaying a virtual ultrasound image; and
a simulation software for simulating the virtual ultrasound image associated with the virtual needle insertion using the position of the simulated syringe from the haptic robotic arm and the position of the ultrasound probe shell from the position tracking sensor and providing performance feedback to the user,
wherein the simulated syringe includes an extendable plunger, the plunger disposed at a proximal end of the syringe and operable to be pulled back for simulating aspiration of the simulated syringe,
wherein the plunger includes a sensor that senses the pullback negative pressure when the user is aspirating the simulated syringe, and
wherein the simulated syringe includes a syringe compartment and the retractable needle is operable to retract into the syringe compartment when pushed against a surface.

17. The virtual haptic training system according to claim 16, wherein:
the motion tracker is operable to receive signals from the position tracking probe and determine the position of the position tracking probe;
the haptic robotic arm, the motion tracker and the scanning pad each have a home position to return to after each trial; and
the position tracking probe includes a shell that mimics a real ultrasound probe.

18. The virtual haptic training system according to claim 16, wherein:
the scanning pad is a phantom tissue made from synthetic material, providing a penetrable, compressible, realistic-feeling scanning surface for the ultrasound; and
the phantom tissue is moldable to any shape to simulate non-planar surfaces on an actual human body.

19. A system, comprising:
a central system;
a plurality of virtual haptic training systems in accordance with claim 16, each of the plurality of virtual haptic training systems communicably connected to the central system;
wherein the central system is configured to allow for continual collection of learning information from the plurality of virtual haptic training systems and continual simulation updates to be made to each of the plurality of virtual haptic training systems to allow for continuous learning efficiency improvement.

20. A method for a virtual haptic training, the method comprising the steps of:
providing a virtual haptic training system including:
a haptic robotic arm having a holster, the haptic robotic arm providing position data to the system and force feedback to a user;
a simulated tool, attached to the holster of the robotic arm, a position of the simulated tool tracked by the haptic robotic arm;
a position tracking system including a virtual ultrasound probe and a motion tracker, the virtual ultrasound probe being a position tracking probe outfitted as an ultrasound probe;
a scanning pad having a surface for the user to perform virtual ultrasound probing and virtual tool manipulation;
a monitor for display; and
a computer having a simulation software;
performing a virtual tool manipulation by moving the simulated tool across the scanning surface and engaging the surface of the scanning pad;
providing the position of the simulated tool by the haptic robotic arm during the performing of the virtual tool manipulation;

performing a virtual ultrasound probing across the surface of the scanning pad;

providing the position of the virtual ultrasound probe by the position tracking system during the performing of the virtual ultrasound probing;

simulating, by the computer, a virtual ultrasound image associated with the virtual tool manipulation using the position of the simulated tool and the position of the virtual ultrasound probe; and displaying a virtual ultrasound visualization associated with the virtual tool manipulation on the monitor and providing performance feedback to a user, wherein the scanning pad is made from phantom tissue, and wherein the virtual ultrasound visualization is a virtual environment created based on a number of actual ultrasound images, and the virtual environment includes a background of the virtual ultrasound created as a static compilation of ultrasound images taken from a region around a vein, and the virtual environment includes two circles and virtual vessel images are created by overlaying the images of an artery and the vein onto the circles providing images of a virtual vein and a virtual artery.

21. The method according to claim 20, wherein pressing the virtual ultrasound probe into the scanning pad surface causes the virtual vein to compress, thereby simulating a real ultrasound procedure.

22. The method according to claim 20, wherein the virtual vein is differentiated from the virtual artery by checking their respective compressibility.

23. The method according to claim 20, wherein a colored bar appears on the virtual image representing blood flash when the virtual needle enters a virtual vessel, the color depending on whether the virtual vessel is the virtual vein or virtual artery.

24. The method according to claim 20, wherein the virtual artery image has a pulsatile nature to represent a heartbeat.

\* \* \* \* \*